(12) United States Patent
Elomari

(10) Patent No.: US 9,539,545 B2
(45) Date of Patent: Jan. 10, 2017

(54) PROCESSES USING MOLECULAR SIEVE SSZ-96

(71) Applicant: Saleh Ali Elomari, Fairfield, CA (US)

(72) Inventor: Saleh Ali Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 381 days.

(21) Appl. No.: 14/283,730

(22) Filed: May 21, 2014

(65) Prior Publication Data

US 2015/0104364 A1  Apr. 16, 2015

Related U.S. Application Data

(60) Provisional application No. 61/889,877, filed on Oct. 11, 2013.

(51) Int. Cl.
| | | |
|---|---|---|
| C07C 15/02 | (2006.01) | |
| B01D 53/94 | (2006.01) | |
| C07C 209/16 | (2006.01) | |
| C07C 2/66 | (2006.01) | |
| C10G 47/04 | (2006.01) | |
| C10G 45/12 | (2006.01) | |
| B01D 53/22 | (2006.01) | |
| C01B 37/02 | (2006.01) | |
| C01B 39/48 | (2006.01) | |
| C07C 1/20 | (2006.01) | |
| C10G 29/20 | (2006.01) | |
| C10G 35/06 | (2006.01) | |
| C10G 45/00 | (2006.01) | |
| C10G 45/54 | (2006.01) | |
| C10G 45/64 | (2006.01) | |
| C10G 45/68 | (2006.01) | |
| C10G 47/16 | (2006.01) | |
| C10G 49/08 | (2006.01) | |
| C10G 2/00 | (2006.01) | |
| C10G 3/00 | (2006.01) | |
| C10G 11/05 | (2006.01) | |
| C07C 5/27 | (2006.01) | |
| C07C 6/12 | (2006.01) | |
| B01J 29/70 | (2006.01) | |

(52) U.S. Cl.
CPC ......... B01D 53/9486 (2013.01); B01D 53/228 (2013.01); B01D 53/9413 (2013.01); B01D 53/9418 (2013.01); B01J 29/70 (2013.01); C01B 37/02 (2013.01); C01B 39/48 (2013.01); C07C 1/20 (2013.01); C07C 2/66 (2013.01); C07C 5/2708 (2013.01); C07C 6/126 (2013.01); C07C 209/16 (2013.01); C10G 2/334 (2013.01); C10G 3/49 (2013.01); C10G 11/05 (2013.01); C10G 29/205 (2013.01); C10G 35/065 (2013.01); C10G 45/00 (2013.01); C10G 45/12 (2013.01); C10G 45/54 (2013.01); C10G 45/64 (2013.01); C10G 45/68 (2013.01); C10G 47/04 (2013.01); C10G 47/16 (2013.01); C10G 49/08 (2013.01); *B01D 2253/116* (2013.01); *B01D 2255/50* (2013.01); *B01D 2257/404* (2013.01); *B01D 2257/702* (2013.01); *B01D 2258/01* (2013.01); *C07C 2529/70* (2013.01); *C10G 2300/70* (2013.01); *Y02C 20/20* (2013.01); *Y02P 30/20* (2015.11)

(58) Field of Classification Search
CPC .......... C07C 15/02; C07C 1/20; C07C 209/16; C07C 2/66; C07C 5/2708; C07C 6/126; C07C 11/02; C07C 15/08; C07C 211/04; C07C 2529/70; B01D 2253/116; B01D 2255/50; B01D 2257/404; B01D 2257/702; B01D 2258/01; B01D 53/228; B01D 53/9413; B01D 53/9418; B01D 53/9486; B01J 29/70; C01B 37/02; C01B 39/48
USPC ........ 208/112, 216 R, 60; 423/212; 585/269, 585/275, 419, 467, 469, 481, 500, 531, 585/640, 666, 733
See application file for complete search history.

(56) References Cited

U.S. PATENT DOCUMENTS

| | | | |
|---|---|---|---|
| 4,297,328 A | 10/1981 | Ritscher et al. | |
| 4,524,234 A | 6/1985 | Kaiser | |
| 7,309,558 B1 | 12/2007 | Michel et al. | |
| 8,545,801 B1 | 10/2013 | Zones | |
| 2008/0159936 A1 | 7/2008 | Zones et al. | |
| 2008/0159950 A1 | 7/2008 | Miller et al. | |
| 2008/0300425 A1 | 12/2008 | Yuen et al. | |

FOREIGN PATENT DOCUMENTS

WO     2008042979     4/2008

OTHER PUBLICATIONS

PCT International Search Report, PCT/US2014/038958, mailed Nov. 6, 2014.

*Primary Examiner* — Sharon Pregler
(74) *Attorney, Agent, or Firm* — Terrence M. Flaherty

(57) ABSTRACT

The present disclosure is directed to processes using a new crystalline molecular sieve designated SSZ-96, which is synthesized using a 1-butyl-1-methyl-octahydroindolium cation as a structure directing agent.

10 Claims, 2 Drawing Sheets

PROCESSES USING MOLECULAR SIEVE SSZ-96

TECHNICAL FIELD

The present disclosure relates to processes using a new molecular sieve designated SSZ-96, wherein the molecular sieve is synthesized using a 1-butyl-1-methyl-octahydroindolium cation as a structure directing agent ("SDA").

BACKGROUND

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY

The present disclosure is directed to a family of crystalline molecular sieves with unique properties, referred to herein as "molecular sieve SSZ-96" or simply "SSZ-96."

In one aspect, there is provided a molecular sieve having a mole ratio of at least 10 of (1) at least one oxide of at least one tetravalent element to (2) optionally, one or more oxides selected from the group consisting of oxides of trivalent elements, pentavalent elements, and mixtures thereof, and having, in its calcined form, the X-ray diffraction lines of Table 6. It should be noted that the phrase "mole ratio of at least 10" includes the case where there is no oxide (2), i.e., the mole ratio of oxide (1) to oxide (2) is infinity. In that case, the molecular sieve is comprised of essentially all of the oxide of the one or more tetravalent elements.

In another aspect, there is provided a method of preparing a crystalline molecular sieve by contacting under crystallization conditions (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; and (5) a 1-butyl-1-methyl-octahydroindolium cation.

In yet another aspect, there is provided a process for preparing a crystalline molecular sieve having, in its calcined form, the X-ray diffraction lines of Table 6, by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) a 1-butyl-1-methyl-octahydroindolium cation, and (6) water; and (b) maintaining the reaction mixture under crystallization conditions sufficient to form crystals of the molecular sieve.

The present disclosure also provides SSZ-96 molecular sieves having a composition, as-synthesized and in the anhydrous state, in terms of mole ratios, as follows:

|  | Broad | Exemplary |
| --- | --- | --- |
| $TO_2/X_2O_n$ | ≥10 | 20 to 100 |
| $Q/TO_2$ | 0.05 to 0.5 | 0.1 to 0.3 |
| $M/TO_2$ | 0.01 to 0.6 | 0.02 to 0.35 | wherein: (1) T is selected from the group consisting of tetravalent elements from Groups 4-14 of the Periodic Table, and mixtures thereof; (2) X is selected from the group consisting of trivalent and pentavalent elements from Groups 3-13 of the Periodic Table, and mixtures thereof; (3) stoichiometric variable n equals the valence state of compositional variable X (e.g., when X is trivalent, n=3; when X is pentavalent, n=5); (4) Q is a 1-butyl-1-methyl-octahydroindolium cation; and (5) M is selected from the group consisting of elements from Groups 1 and 2 of the Periodic Table.

DETAILED DESCRIPTION

Introduction

Figure 1:
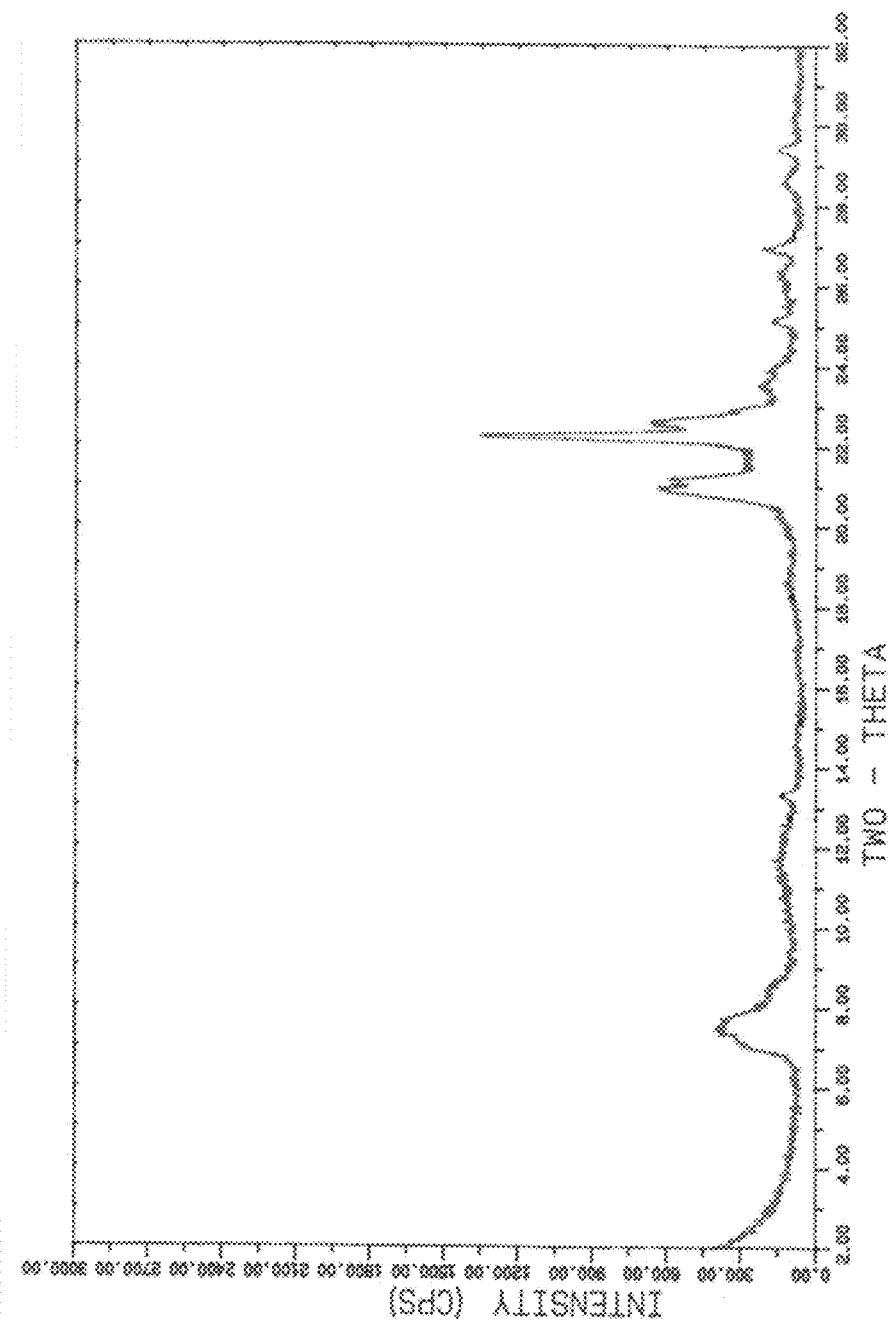
FIG. 1 is a powder X-ray diffraction (XRD) pattern of the as-synthesized molecular sieve prepared in Example 2.

The following terms will be used throughout the specification and will have the following meanings unless otherwise indicated.

The term "active source" means a reagent or precursor material capable of supplying at least one element in a form that can react and which can be incorporated into the molecular sieve structure. The terms "source" and "active source" can be used interchangeably herein.

The term "Periodic Table" refers to the version of IUPAC Periodic Table of the Elements dated Jun. 22, 2007, and the numbering scheme for the Periodic Table Groups is as described in *Chem. Eng. News*, 63(5), 26-27 (1985).

In preparing SSZ-96, a 1-butyl-1-methyl-octahydroindolium cation is used as a structure directing agent ("SDA"), also known as a crystallization template. The SDA useful for making SSZ-96 is represented by the following structure (1):

(1)

The SDA cation is associated with anions which can be any anion that is not detrimental to the formation of SSZ-96. Representative anions include elements from Group 17 of the Periodic Table (e.g., fluoride, chloride, bromide and iodide), hydroxide, acetate, sulfate, tetrafluoroborate, carboxylate, and the like.

Reaction Mixture

In general, SSZ-96 is prepared by: (a) preparing a reaction mixture containing (1) at least one source of an oxide of at least one tetravalent element; (2) optionally, one or more sources of one or more oxides selected from the group consisting of oxides of trivalent elements, pentavalent elements, and mixtures thereof; (3) at least one source of an element selected from Groups 1 and 2 of the Periodic Table; (4) hydroxide ions; (5) a 1-butyl-1-methyl-octahydroindolium cation; and (6) water; and (b) maintaining the reaction mixture under crystallization conditions sufficient to form crystals of the molecular sieve.

The composition of the reaction mixture from which the molecular sieve is formed, in terms of mole ratios, is identified in Table 1 below, wherein compositional variables T, X, M, and Q and stoichiometric variable n are as described herein above.

TABLE 1

| Components | Broad | Exemplary |
|---|---|---|
| $TO_2/X_2O_n$ | ≥10 | 20 to 100 |
| $M/TO_2$ | 0.01 to 1.0 | 0.02 to 0.35 |
| $Q/TO_2$ | 0.05 to 0.5 | 0.1 to 0.3 |
| $OH/TO_2$ | 0.1 to 1.0 | 0.2 to 0.6 |
| $H_2O/TO_2$ | 10 to 100 | 20 to 50 |

In one sub-embodiment, the composition of the reaction mixture from which SSZ-96 is formed, in terms of mole ratios, is identified in Table 2 below, wherein compositional variables M and Q are as described herein above.

TABLE 2

| Components | Broad | Exemplary |
|---|---|---|
| $SiO_2/Al_2O_3$ | ≥10 | 20 to 100 |
| $M/SiO_2$ | 0.01 to 1.0 | 0.02 to 0.35 |
| $Q/SiO_2$ | 0.05 to 0.5 | 0.1 to 0.3 |
| $OH/SiO_2$ | 0.1 to 1.0 | 0.2 to 0.6 |
| $H_2O/SiO_2$ | 10 to 100 | 20 to 50 |

As noted above, for each embodiment described herein, T is selected from the group consisting of tetravalent elements from Groups 4-14 of the Periodic Table. In one sub-embodiment, T is selected from the group consisting of silicon (Si), germanium (Ge), titanium (Ti), and mixtures thereof. In another sub-embodiment, T is selected from the group consisting of Si, Ge, and mixtures thereof. In one sub-embodiment, T is Si. Sources of elements selected for composition variable T include oxides, hydroxides, acetates, oxalates, ammonium salts and sulfates of the element(s) selected for T. In one sub-embodiment, each source(s) of the element(s) selected for composition variable T is an oxide. Where T is Si, sources useful for Si include fumed silica, precipitated silicates, silica hydrogel, silicic acid, colloidal silica, tetra-alkyl orthosilicates (e.g., tetraethyl orthosilicate), and silica hydroxides. Sources useful herein for Ge include germanium oxide and germanium ethoxide.

For each embodiment described herein, X is selected from the group consisting of elements from Groups 3-13 of the Periodic Table. In one sub-embodiment, X is selected from the group consisting of boron (B), aluminum (Al), gallium (Ga), indium (In), iron (Fe), and mixtures thereof. In another sub-embodiment, X is selected from the group consisting of B, Al, Ga, In, and mixtures thereof. In one sub-embodiment X is Al. Sources of elements selected for optional composition variable X include oxides, hydroxides, acetates, oxalates, ammonium salts and sulfates of the element(s) selected for X. Where X is Al, sources useful for Al include aluminates, alumina, and aluminum compounds such as $AlCl_3$, $Al_2(SO_4)_3$, $Al(OH)_3$, kaolin clays, and other zeolites. An example of the source of aluminum oxide is LZ-210 zeolite (a type of Y zeolite). Boron, gallium, and iron can be added in forms corresponding to their aluminum and silicon counterparts.

As described herein above, for each embodiment described herein, the reaction mixture can be formed using at least one source of an element selected from Groups 1 and 2 of the Periodic Table (referred to herein as M). In one sub-embodiment, the reaction mixture is formed using a source of an element from Group 1 of the Periodic Table. In another sub-embodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halides, oxalates, citrates and acetates thereof.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization and Post-Synthesis Treatment

In practice, the molecular sieve is prepared by: (a) preparing a reaction mixture as described herein above; and (b) maintaining the reaction mixture under crystallization conditions sufficient to form crystals of the molecular sieve.

The reaction mixture is maintained at an elevated temperature until the crystals of the molecular sieve are formed. The hydrothermal crystallization is usually conducted under pressure, and usually in an autoclave so that the reaction mixture is subject to autogenous pressure, at a temperature between 125° C. and 200° C.

The reaction mixture can be subjected to mild stirring or agitation during the crystallization step. It will be understood by one skilled in the art that the molecular sieves described herein can contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for compositional variable T used in the reaction mixture.

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by photolysis techniques (e.g., exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327.

The molecular sieve can subsequently be calcined in steam, air or inert gas at temperatures ranging from 200° C. to 800° C. for periods of time ranging from 1 to 48 hours, or more. Usually, it is desirable to remove the extra-framework cation (e.g., Na$^+$) by ion exchange and replace it with hydrogen, ammonium, or any desired metal-ion.

Where the molecular sieve formed is an intermediate molecular sieve, the target molecular sieve can be achieved using post-synthesis techniques such as heteroatom lattice substitution techniques. The target molecular sieve (e.g., silicate SSZ-96) can also be achieved by removing heteroatoms from the lattice by known techniques such as acid leaching.

The molecular sieve made from the process disclosed herein can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying or dried (or partially dried) and then extruded.

The molecular sieve can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. Nos. 4,910,006 and 5,316,753.

SSZ-96 is useful in catalysts for a variety of hydrocarbon conversion reactions such as hydrocracking, dewaxing, olefin isomerization, alkylation of aromatic compounds and the like. SSZ-96 is also useful as an adsorbent for separations.

Characterization of the Molecular Sieve

Molecular sieves made by the process disclosed herein have a composition, as-synthesized and in the anhydrous state, as described in Table 3 (in terms of mole ratios), wherein compositional variables T, X, Q and M and stoichiometric variable n are as described herein above:

TABLE 3

|  | Broad | Exemplary |
| --- | --- | --- |
| $TO_2/X_2O_n$ | ≥10 | 20 to 100 |
| $Q/TO_2$ | 0.05 to 0.5 | 0.1 to 0.3 |
| $M/TO_2$ | 0.01 to 0.6 | 0.02 to 0.35 |

In one sub-embodiment, the molecular sieves made by the process of the disclosed herein have a composition, as-synthesized and in the anhydrous state, as described in Table 4 (in terms of mole ratios), wherein compositional variables Q and M are as described herein above:

TABLE 4

|  | Broad | Exemplary |
| --- | --- | --- |
| $SiO_2/Al_2O_3$ | ≥10 | 20 to 100 |
| $Q/SiO_2$ | 0.05 to 0.5 | 0.1 to 0.3 |
| $M/SiO_2$ | 0.01 to 0.6 | 0.02 to 0.35 |

Molecular sieves synthesized by the process disclosed herein can be characterized by their XRD pattern. The powder XRD lines of Table 5 are representative of as-synthesized SSZ-96 made in accordance with the method described herein. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

TABLE 5

Characteristic Peaks for As-Synthesized SSZ-96

| 2-Theta[a] | d-spacing (nm) | Relative Intensity[b] |
| --- | --- | --- |
| 7.60 | 1.162 | S |
| 8.47 | 1.043 | W |
| 21.00 | 0.423 | S |
| 22.28 | 0.399 | VS |
| 22.66 | 0.392 | VS |
| 23.64 | 0.376 | W |
| 25.20 | 0.353 | W |
| 26.94 | 0.331 | W |
| 28.60 | 0.312 | W |
| 29.48 | 0.303 | W |
| 33.20 | 0.270 | W |
| 37.80 | 0.238 | W |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The X-ray diffraction pattern lines of Table 6 are representative of calcined SSZ-96 made in accordance with the method described herein.

TABLE 6

Characteristic Peaks for Calcined SSZ-96

| 2-Theta[a] | d-spacing (nm) | Relative Intensity[b] |
| --- | --- | --- |
| 7.50 | 1.178 | VS |
| 8.52 | 1.037 | M |
| 14.50 | 0.610 | W |
| 20.86 | 0.425 | S |
| 22.26 | 0.399 | VS |
| 22.76 | 0.390 | S |
| 23.60 | 0.377 | W |
| 24.02 | 0.370 | W |
| 25.16 | 0.354 | W |
| 26.40 | 0.337 | W |
| 26.94 | 0.331 | W |
| 28.57 | 0.312 | W |
| 29.41 | 0.303 | W |

[a]±0.20
[b]The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Hydrocarbon Conversion Processes

SSZ-96 is useful as catalyst in a wide range of hydrocarbon conversion processes. Hydrocarbon conversion reactions are chemical and catalytic processes in which carbon-containing compounds are changed to different carbon-containing compounds. Specific examples of hydrocarbon conversion processes which are effectively catalyzed by SSZ-96, by itself or in combination with one or more other catalytically active substances including other crystalline catalysts, include hydrocracking, dewaxing, catalytic cracking, aromatics formation, isomerization, alkylation and transalkylation, conversion of paraffins to aromatics, isomerization of olefins, xylene isomerization, oligomerization, condensation of alcohols, methane upgrading and polymerization of 1-olefins.

The SSZ-96 catalysts can have high selectivity, and under hydrocarbon conversion conditions can provide a high percentage of desired products relative to total products.

For high catalytic activity, SSZ-96 should be predominantly in its hydrogen ion form. Generally, the molecular sieve is converted to its hydrogen form by ammonium exchange followed by calcination. If the molecular sieve is synthesized with a high enough ratio of SDA cation to sodium ion, calcination alone can be sufficient. Typically, after calcination at least 80% of the cation sites are occupied by hydrogen ions and/or rare earth ions. As used herein, "predominantly in the hydrogen form" means that, in its calcined form, at least 80% of the cation sites of the molecular sieve are occupied by hydrogen ions and/or rare earth ions.

SSZ-96 can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sands oil, synthetic paraffins from NAO, recycled plastic feedstocks. Other feeds include synthetic feeds, such as those derived from a Fischer-Tropsch process, including an oxygenate-containing Fischer-Tropsch process boiling below about 371° C. In general, the feed can be any carbon-containing feedstock susceptible to zeolitic catalytic reactions. Depending on the type of processing the hydrocarbonaceous feed is to undergo, the feed can contain metal or be free of metals; it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

The following Table 7 indicates typical reaction conditions which can be employed when using catalysts comprising SSZ-96 in the hydrocarbon conversion reactions disclosed herein. Typical conditions are indicated in parentheses.

TABLE 7

| Process | Temperature (° C.) | Pressure (MPa) | LHSV (h$^{-1}$) |
| --- | --- | --- | --- |
| Hydrocracking | 175 to 485 | 0.05 to 35 | 0.1 to 30 |
| Catalytic Cracking | 127 to 885 | (0.1 to 0.5) | 0.5 to 50 |
| Dewaxing | 200 to 475 (250 to 450) | 0.10 to 20.7[1] (1.38 to 20.7)[1] | 0.1 to 20 (0.2 to 10) |
| Aromatics Formation | 400 to 600 (480 to 550) | 0.1 to 1 | 0.1 to 15 |
| Paraffins to Aromatics | 100 to 700 | 0 to 6.89[1] | 0.5 to 40[5] |
| Isomerization | 93 to 538 (204 to 315) | 0.34 to 6.89[1] | 1 to 10 (1 to 4) |
| Xylene Isomerization | 260 to 593[2] (315 to 566)[2] 38 to 371[4] | 0.05 to 5.1[2] (0.1 to 0.51)[2] 0.1 to 20.3[4] | 0.1 to 100[5] (0.5 to 50)[5] 0.5 to 50 |
| Oligomerization | 232 to 649[2] 10 to 232[4] (27 to 204)[4] | 0.01 to 5.1[2,3] | 0.2 to 50[2] 0.05 to 20[5] (0.1 to 10)[5] |
| Condensation of Alcohols | 260 to 538 | 0.0034 to 6.89[1] | 0.5 to 50[5] |

[1]Gauge pressure, i.e., the absolute pressure minus the ambient pressure
[2]Gas-phase reaction
[3]Hydrocarbon partial pressure
[4]Liquid-phase reaction
[5]Weight Hourly Space Velocity (WHSV)

Other reaction conditions and parameters are provided below.

Hydrocracking

Using a catalyst which comprises SSZ-96 (e.g., predominantly in the hydrogen form) and a hydrogenation promoter, heavy petroleum residual feedstocks, cyclic stocks and other hydrocrackate charge stocks can be hydrocracked using the process conditions and catalyst components disclosed in U.S. Pat. Nos. 4,910,006 and 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Groups 6 and 8-10 of the Periodic Table, including the salts, complexes and solutions containing such. The hydrogenation catalyst can be selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, for example in the range of from 0.05 to 25 wt. %.

Catalytic Cracking

Hydrocarbon cracking stocks can be catalytically cracked in the absence of hydrogen using SSZ-96, for example predominantly in the hydrogen form.

When SSZ-96 is used as a catalytic cracking catalyst in the absence of hydrogen, the catalyst can be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. Nos. 4,910,006 and 5,316,753. When a traditional cracking catalyst component is employed, the relative weight ratio of the traditional cracking catalyst component to the SSZ-96 is generally from 1:10 to 500:1, e.g., from 1:10 to 200:1, from 1:2 to 50:1, or from 1:1 to 20:1. SSZ-96 and/or the traditional cracking component can be further ion exchanged with rare earth ions to modify selectivity.

The cracking catalysts are typically employed with an inorganic oxide matrix component. See the aforementioned U.S. Pat. Nos. 4,910,006 and 5,316,753 for examples of such matrix components.

Hydrotreating

SSZ-96 is useful as a hydrotreating catalyst. During hydrotreatment, oxygen, sulfur and nitrogen present in a hydrocarbonaceous feed is reduced to low levels. Aromatics and olefins, if present in the feed, can also have their double bonds saturated. In some cases, the hydrotreating catalyst and hydrotreating conditions are selected to minimize cracking reactions, which can reduce the yield of the most desulfided product (typically useful as a fuel).

Hydrotreating conditions typically include a reaction temperature of from 204° C. to 482° C., e.g., from 343° C. to 454° C.; a pressure of from 500 to 5000 psig (3.5 to 34.5 MPa), e.g., from 1000 to 3000 psig (6.89 to 20.7 MPa); a liquid hourly space velocity (LHSV) of from 0.5 to 20 $h^{-1}$ (v/v); and an overall hydrogen consumption of from 300 to 2000 SCF/bbl (standard cubic feet per barrel) of liquid hydrocarbon feed (53.4 to 356 $m^3$ $H_2/m^3$ feed). The hydrotreating catalyst will typically be a composite of a Group 6 metal or compound thereof and a Group 8-10 metal or compound thereof supported on the molecular sieve disclosed herein. Typically, such hydrotreating catalysts are presulfided.

Catalysts useful for hydrotreating hydrocarbon feeds are disclosed in U.S. Pat. Nos. 4,347,121 and 4,810,357. Suitable catalysts include noble metals from Group 8-10 of the Periodic Table, such as iron, cobalt, nickel, platinum or palladium, and/or Group 6 metals, such as chromium, molybdenum, or tungsten. Examples of combinations of Group 8-10 and Group 6 metals include Ni—Mo or Ni—W. Other suitable catalysts are described in U.S. Pat. Nos. 3,904,513 and 4,157,294. U.S. Pat. No. 3,852,207 describes suitable noble metal catalysts and mild hydrotreating conditions.

The amount of hydrogenation component(s) in the catalyst suitably range from 0.5 to 10 wt. % of Group 8-10 component(s) and from 5 to 25 wt. % of Group 6 metal component(s), calculated as metal oxide(s) per 100 parts by weight of total catalyst, where the percentages by weight are based on the weight of the catalyst before sulfiding. The hydrogenation component(s) in the catalyst can be in the oxide and/or sulfide form.

Dewaxing

SSZ-96, for example predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-96 under isomerization dewaxing conditions.

The catalytic dewaxing conditions are dependent in large measure on the feed used and upon the desired pour point. Hydrogen is typically present in the reaction zone during the catalytic dewaxing process. The hydrogen to feed ratio is typically from 500 to 30,000 SCF/bbl (0.089 to 5.34 SCM/L (standard cubic meters/liter)), e.g., from 1000 to 20,000 SCF/bbl (0.178 to 3.56 SCM/L). Generally, hydrogen will be separated from the product and recycled to the reaction zone. Typical feedstocks include light gas oil, heavy gas oils and reduced crudes boiling above about 177° C.

A typical dewaxing process is the catalytic dewaxing of a hydrocarbon oil feedstock boiling above about 177° C. and containing straight chain and slightly branched chain hydrocarbons by contacting the hydrocarbon oil feedstock in the presence of added hydrogen gas at a hydrogen pressure of from 15 to 3000 psi (103 kPa to 20.7 MPa) with a catalyst comprising SSZ-96 and at least one Group 8-10 metal. The term "Group 8-10 metal" as used herein is meant the metal itself or a compound thereof.

The SSZ-96 dewaxing catalyst can optionally contain a hydrogenation component of the type commonly employed in dewaxing catalysts. See the aforementioned U.S. Pat. Nos. 4,910,006 and 5,316,753 for examples of these hydrogenation components.

The hydrogenation component is present in an effective amount to provide an effective hydrodewaxing and hydroisomerization catalyst, for example in the range of from 0.05 to 5 wt. %. The catalyst can be run in such a mode to increase isomerization dewaxing at the expense of cracking reactions.

The feed can be hydrocracked, followed by dewaxing. This type of two stage process and typical hydrocracking conditions are described in U.S. Pat. No. 4,921,594.

SSZ-96 can also be utilized as a dewaxing catalyst in the form of a combination of catalysts. The combination comprises a first catalyst comprising SSZ-96 and, desirably, at least one metal selected from Groups 8-10 of the Periodic Table, and a second catalyst comprising an aluminosilicate zeolite which is more shape selective than SSZ-96. As used herein, the term "combination" includes mixtures of SSZ-96 and the aluminosilicate zeolite, layers of SSZ-96 and the zeolite, or any other configuration in which the feed comes in contact with both SSZ-96 and the zeolite. The use of combined catalysts in the form of layers is disclosed in U.S. Pat. No. 5,149,421. The layering can also include a bed of SSZ-96 layered with a non-zeolitic component designed for either hydrocracking or hydrofinishing.

SSZ-96 can also be used to dewax raffinates, including bright stock, under conditions such as those disclosed in U.S. Pat. No. 4,181,598.

It is often desirable to use mild hydrogenation (sometimes referred to as hydrofinishing) to produce more stable dewaxed products. The hydrofinishing step can be performed either before or after the dewaxing step, typically after. Hydrofinishing is typically conducted at a temperature ranging from 190° C. to 340° C., at a pressure ranging from 400 to 3000 psig (2.76 to 20.7 MPa), at a LHSV ranging from 0.1 and 20 $h^{-1}$ and a hydrogen recycle rate ranging from 400 to 1500 SCF/bbl (0.071 to 0.27 SCM/L). The hydrogenation catalyst employed must be active enough not only to hydrogenate the olefins, di-olefins and color bodies which can be present, but also to reduce the aromatic content. Suitable hydrogenation catalysts are disclosed in U.S. Pat. No. 4,921,594. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil can be prepared using SSZ-96. For example, a $C_{20+}$ lube oil can be made by isomerizing a $C_{20+}$ olefin feed over a catalyst comprising SSZ-96 in the hydrogen form and at least one metal selected from Groups 8-10 of the Periodic Table. Alternatively, the lubricating oil can be made by hydrocracking in a hydrocracking zone a hydrocarbonaceous feedstock to obtain an effluent comprising a hydrocracked oil, and catalytically dewaxing the effluent at a temperature of at least 204° C. and at a pressure of from 15 to 3000 psig (103 kPa to 20.7 MPa) in the presence of added hydrogen gas with a catalyst comprising SSZ-96 in the hydrogen form and at least one metal selected from Groups 8-10 of the Periodic Table.

Hydrogenation

SSZ-96 can be used in a catalyst to catalyze hydrogenation of a hydrocarbon feed containing unsaturated hydrocarbons. The unsaturated hydrocarbons can comprise olefins, dienes, polyenes, aromatic compounds and the like.

Hydrogenation is accomplished by contacting the hydrocarbon feed containing unsaturated hydrocarbons with hydrogen in the presence of a catalyst comprising SSZ-96. The catalyst can also contain one or more metals of Group 6 and Group 8-10, including salts, complexes and solutions thereof. Reference to these catalytically active metals is intended to encompass such metals or metals in the elemental state or in some form such as an oxide, sulfide, halide, carboxylate and the like. Examples of such metals include metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

The hydrogenation component of the catalyst (i.e., the aforementioned metal) is present in an amount effective to provide the hydrogenation function of the catalyst, e.g., in the range of from 0.05 to 25 wt. %.

Hydrogenation conditions, such as temperature, pressure, space velocities, contact time and the like are well known in the art.

Methane Upgrading

Higher molecular weight hydrocarbons can be formed from lower molecular weight hydrocarbons by contacting the lower molecular weight hydrocarbon with a catalyst comprising SSZ-96 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. Nos. 4,734,537; 4,939,311; 4,962,261; 5,095,161; 5,105,044; 5,105,046; 5,238,898; 5,321,185; and 5,336,825.

Aromatics Formation

SSZ-96 can be used to convert light straight run naphthas and similar mixtures to highly aromatic mixtures. Thus, normal and slightly branched chained hydrocarbons having a boiling range above 40° C. and less than 200° C. can be converted to products having substantially higher octane aromatics content by contacting the hydrocarbon feed with a catalyst comprising SSZ-96. It is also possible to convert heavier feeds into BTX or naphthalene derivatives of value using a catalyst comprising SSZ-96.

The conversion catalyst typically contains a Group 8-10 metal compound to have sufficient activity for commercial use. The Group 8-10 noble metals and their compounds, platinum, palladium, and iridium, or combinations thereof can be used. Rhenium or tin or a mixture thereof can also be used in conjunction with the Group 8-10 metal compound (typically a noble metal compound), for example a platinum compound. The amount of Group 8-10 metal present in the conversion catalyst should be within the normal range of use in reforming catalysts, e.g., from 0.05 to 2.0 wt. %, or from 0.2 to 0.8 wt. %.

For the selective production of aromatics in useful quantities, it is desirable that the conversion catalyst be substantially free of acidity, for example, by neutralizing the molecular sieve with a basic metal, e.g., an alkali metal compound. Methods for rendering the catalyst free of acidity are known in the art. See the aforementioned U.S. Pat. Nos. 4,910,006 and 5,316,753 for a description of such methods.

Typical alkali metals are sodium, potassium, rubidium and cesium. The molecular sieve itself can be substantially free of acidity only at very high silica to alumina mole ratios.

Conversion of Paraffins to Aromatics

SSZ-96 can be used to convert light gas $C_2$ to $C_6$ paraffins to higher molecular weight hydrocarbons including aromatic compounds. Typically, the molecular sieve will contain a catalyst metal or metal oxide wherein the metal is selected from the group consisting of Groups 3, 8-10, 11, and 12 of the Periodic Table, e.g., gallium, niobium, indium or zinc, in the range of from 0.05 to 5 wt. %.

Alkylation and Transalkylation

SSZ-96 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-96.

SSZ-96 can also be used for removing benzene from gasoline by alkylating the benzene as described above and removing the alkylated product from the gasoline.

For high catalytic activity, SSZ-96 should be predominantly in its hydrogen ion form. It is typical that, in its calcined form, at least 80% of the cation sites of the molecular sieve are occupied by hydrogen ions and/or rare earth ions.

Examples of suitable aromatic hydrocarbon feedstocks which can be alkylated or transalkylated by the process disclosed herein include aromatic compounds such as benzene, toluene and xylene. Benzene is especially useful. There can be occasions where naphthalene or naphthalene derivatives such as dimethylnaphthalene can be desirable. Mixtures of aromatic hydrocarbons can also be employed.

Suitable olefins for the alkylation of the aromatic hydrocarbon are those containing from 2 to 20 carbon atoms, e.g., from 2 to 4 carbon atoms, such as ethylene, propylene, 1-butene, cis-2-butene and trans-2-butene, or mixtures thereof. There can be instances where pentenes are desirable. Typical olefins are ethylene and propylene. Longer chain alpha-olefins can be used as well.

When transalkylation is desired, the transalkylating agent is a polyalkyl aromatic hydrocarbon containing two or more alkyl groups that each can have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), diisopropylbenzene, diisopropyltoluene, dibutylbenzene, and the like. Typical polyalkyl aromatic hydrocarbons are the dialkylbenzenes. A particularly desirable polyalkyl aromatic hydrocarbon is diisopropylbenzene.

When alkylation is the process conducted, reaction conditions are as follows. The aromatic hydrocarbon feed should be present in stoichiometric excess. It is typical that the molar ratio of aromatics to olefins be greater than four-to-one to prevent rapid catalyst fouling. The reaction temperature can range from 38° C. to 315° C., e.g., from 121° C. to 232° C. The reaction pressure should be sufficient to maintain at least a partial liquid phase in order to retard catalyst fouling. This is typically 50 to 1000 psig (0.345 to 6.89 MPa) depending on the feedstock and reaction temperature. Contact time can range from 10 seconds to 10 hours, but is usually from 5 minutes to an hour. The WHSV, in terms of grams (pounds) of aromatic hydrocarbon and olefin per gram (pound) of catalyst per hour, is generally within the range of 0.5 to 50 $h^{-1}$.

When transalkylation is the process conducted, the molar ratio of aromatic hydrocarbon will generally range from 1:1 to 25:1, e.g., from 2:1 to 20:1. The reaction temperature can range from 38° C. to 315° C., e.g., from 121° C. to 232° C. The reaction pressure should be sufficient to maintain at least a partial liquid phase, typically in the range of from 50 to 1000 psig (345 kPa to 6.89 MPa), e.g., from 300 to 600 psig (2.07 to 4.14 MPa). The WHSV will range from 0.1 to 10 $h^{-1}$. U.S. Pat. No. 5,082,990 describes such processes.

Xylene Isomerization

SSZ-96 can also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream can be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise from 0.1 to 2.0 wt. % of a hydrogenation/dehydrogenation component selected from a Group 8-10 metal component, especially platinum or nickel.

Optionally, the isomerization feed can contain from 10 to 90 wt. % of a diluent such as toluene, trimethylbenzene, naphthenes or paraffins.

Isomerization of $C_4$ to $C_7$ Hydrocarbons

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-96 in the hydrogen form, with a hydrocarbon feed under isomerization conditions. The feed is typically a light straight run fraction, boiling within the range of from –1° C. to 121° C., e.g., from 16° C. to 93° C. Typically, the hydrocarbon feed for the process comprises a substantial amount of $C_4$ to $C_7$ normal and slightly branched low octane hydrocarbons, for example $C_5$ and $C_6$ hydrocarbons.

The isomerization reaction is typically carried out in the presence of hydrogen. Hydrogen can be added to give a hydrogen to hydrocarbon ratio ($H_2$/HC) of from 0.5 to 10 $H_2$/HC, e.g., from 1 and 8 $H_2$/HC. See the aforementioned U.S. Pat. Nos. 4,910,006 and 5,316,753 for a further discussion of isomerization process conditions.

A low sulfur feed is especially useful in the present process. The feed desirably contains less than 10 ppm sulfur, e.g., less than 1 ppm sulfur or less than 0.1 ppm sulfur. In the case of a feed which is not already low in sulfur, acceptable levels can be reached by hydrogenating the feed in a pre-saturation zone with a hydrogenating catalyst which is resistant to sulfur poisoning. See the aforementioned U.S. Pat. Nos. 4,910,006 and 5,316,753 for a further discussion of this hydrodesulfurization process.

It is typical to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. Nos. 4,910,006 and 5,316,753 for a further discussion of methods of removing this sulfur and coke and of regenerating the catalyst.

The conversion catalyst desirably contains a Group 8-10 metal compound to have sufficient activity for commercial use. The Group 8-10 noble metals and their compounds, platinum, palladium, and iridium, or combinations thereof can be used. Rhenium and tin can also be used in conjunction with the noble metal. Typically, the metal is platinum. The amount of Group 8-10 metal present in the conversion catalyst should be within the normal range of use in isomerizing catalysts, e.g., from 0.05 to 2.0 wt. %, or from 0.2 to 0.8 wt. %.

Isomerization of Olefins

SSZ-96 can be used to isomerize olefins. The feed stream is a hydrocarbon stream containing at least one $C_4$ to $C_6$ olefin, e.g., a $C_4$ to $C_6$ normal olefin such as normal butene. Normal butene as used in this specification means all forms of normal butene, e.g., 1-butene, cis-2-butene and trans-2-butene. Typically, hydrocarbons other than normal butene or other $C_4$ to $C_6$ normal olefins will be present in the feed stream. These other hydrocarbons can include alkanes, other olefins, aromatics, hydrogen, and inert gases.

The feed stream typically can be the effluent from a fluid catalytic cracking unit or a methyl-tert-butyl ether (MTBE) unit. A fluid catalytic cracking unit effluent typically contains from 40 to 60 wt. % normal butenes. A MTBE unit effluent typically contains from 40 to 100 wt. % normal butene. The feed stream typically contains at least about 40 wt. % normal butene, e.g., at least 65 wt. % normal butene.

The process is carried out under isomerization conditions. The hydrocarbon feed is contacted in a vapor phase with a catalyst comprising the SSZ-96. The process can be carried out generally at a temperature from 329° C. to 510° C. for butenes, e.g., from 371° C. to 482° C., or from 177° C. to 343° C. for pentenes and hexenes. The pressure ranges from sub-atmospheric to 200 psig (1379 kPa), e.g., from 15 to 200 psig (103 to 1379 kPa) or from 1 to 150 psig (7 to 1034 kPa).

The LHSV during contacting is generally from 0.1 to 50 $h^{-1}$, based on the hydrocarbon feed, e.g., from 0.1 to 20 $h^{-1}$, from 0.2 to 10 $h^{-1}$, or from 1 to 5 $h^{-1}$. A hydrogen/hydrocarbon molar ratio is maintained from about 0 to 30 or higher. The hydrogen can be added directly to the feed stream or directly to the isomerization zone. The reaction is typically substantially free of water, typically less than 2 wt. % based on the feed. The process can be carried out in a packed bed reactor, a fixed bed, fluidized bed reactor, or a moving bed reactor. The bed of the catalyst can move upward or downward. The mole % conversion of, for example, normal butene to iso-butene is at least 10, e.g., at least 25 or at least 35.

Oligomerization of Olefins

It is expected that SSZ-96 can also be used to oligomerize straight and branched chain olefins having from 2 to 21 carbon atoms, e.g., from 2 to 5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-96. The molecular sieve can have the original cations associated therewith replaced by a wide variety of other cations according to techniques well known in the art. Typical cations would include hydrogen, ammonium and metal cations including mixtures of the same. Of the replacing metallic cations, cations of metals such as rare earth metals, manganese, calcium, as well as metals of Group 12 of the Periodic Table, e.g., zinc, and Group 8-10 of the Periodic Table, e.g., nickel are particularly desirable. One of the prime requisites is that the molecular sieve has a fairly low aromatization activity, i.e., in which the amount of aromatics produced is not more than about 20 wt. %. This is accomplished by using a molecular sieve with controlled acid activity (alpha value) of from 0.1 to 120, e.g., from 0.1 to 100, as measured by its ability to crack n-hexane.

Alpha values are defined by a standard test known in the art, e.g., as shown in U.S. Pat. No. 3,960,978. If required, such molecular sieves can be obtained by steaming, by use in a conversion process or by any other method which can occur to one skilled in the art.

Polymerization of 1-Olefins

SSZ-96 can be used in a catalyst for the polymerization of 1-olefins, e.g., the polymerization of ethylene. To form the olefin polymerization catalyst, SSZ-96 is reacted with a particular type of organometallic compound. Organometallic compounds useful in forming the polymerization catalyst include trivalent and tetravalent organotitanium and organochromium compounds having alkyl moieties and, optionally, halide moieties. In the context of the present disclosure, the term "alkyl" includes both straight and branched chain alkyl, cycloalkyl and alkaryl groups such as benzyl.

Examples of trivalent and tetravalent organochromium and organotitanium compounds are disclosed in U.S. Pat. Nos. 4,376,722; 4,377,497; 4,446,243; and 4,526,942.

Examples of the organometallic compounds used to form the polymerization catalyst include, but are not limited to, compounds corresponding to the general formula (2):

$$ZR_cHal_{d-c} \qquad (2)$$

wherein Z is a metal selected from titanium and chromium; R is alkyl; Hal is halogen (e.g., Cl or Br); c is 1-4; and d is greater than or equal to c and is 3 or 4.

Examples of organotitanium and organochromium compounds encompassed by such a formula include compounds of the formula $CrR_4$, $CrR_3$, $CrR_3Hal$, $CrR_2Hal$, $CrR_2Hal_2$, $CrRHal_2$, $CrRHal_3$, $TiR_4$, $TiR_3$, $TiR_3Hal$, $TiR_2Hal$, $TiR_2Hal_2$, $TiRHal_2$, $TiRHal_3$, wherein Hal can be Cl or Br and R can be methyl, ethyl, propyl, isopropyl, butyl, isobutyl, sec-butyl, tert-butyl, pentyl, isopentyl, neopentyl, hexyl, isohexyl, neohexyl, 2-ethybutyl, octyl, 2-ethylhexyl, 2,2-diethylbutyl, 2-isopropyl-3-methylbutyl, etc., cyclohexylalkyls such as, for example, cyclohexylmethyl, 2-cyclohexylethyl, 3-cyclohexylpropyl, 4-cyclohexylbutyl, and the corresponding alkyl-substituted cyclohexyl radicals as, for example, (4-methylcyclohexyl)methyl, neophyl, i.e., β,β-dimethyl-phenethyl, benzyl, ethylbenzyl, and p-isopropylbenzyl.

The organotitanium and organochromium materials employed in the catalyst can be prepared by techniques well known in the art. See, for example the aforementioned U.S. Pat. Nos. 4,376,722; 4,377,497; 4,446,243; and 4,526,942.

The organotitanium or organochromium compounds can be with SSZ-96 such as by reacting the organometallic compound and the molecular sieve, in order to form the olefin polymerization catalyst. Generally, such a reaction takes place in the same reaction medium used to prepare the organometallic compound under conditions which promote formation of such a reaction product. The molecular sieve can simply be added to the reaction mixture after formation of the organometallic compound has been completed. Molecular sieve is added in an amount sufficient to provide from 0.1 to 10 parts by weight, e.g., from 0.5 to 5 parts by weight, of organometallic compound in the reaction medium per 100 parts by weight of molecular sieve.

Temperature of the reaction medium during reaction of organometallic compound with molecular sieve is also maintained at a level which is low enough to ensure the stability of the organometallic reactant. Thus, temperatures in the range of from −150° C. to 50° C., e.g., from −80° C. to 0° C. can be usefully employed. Reaction times of from 0.01 to 10 hours, e.g., from 0.1 to 1 hour, can be employed in the reaction of the organotitanium or organochromium compound with the molecular sieve.

Upon completion of the reaction, the catalyst material so formed can be recovered and dried by evaporating the reaction medium solvent under a nitrogen atmosphere. Alternatively, olefin polymerization reactions can be conducted in this same solvent-based reaction medium used to form the catalyst.

The polymerization catalyst can be used to catalyze polymerization of 1-olefins. The polymers produced using the catalysts of this disclosure are normally solid polymers of at least one mono-1-olefin containing from 2 to 8 carbon atoms per molecule. These polymers are normally solid homopolymers of ethylene or copolymers of ethylene with another mono-1-olefin containing 3 to 8 carbon atoms per molecule. Exemplary copolymers include those of ethylene/propylene, ethylene/1-butene, ethylene/1-hexane, and ethylene/1-octene and the like. The major portion of such copolymers is derived from ethylene and generally consists of from 80 to 99 mol % ethylene, e.g., from 95 to 99 mol % ethylene. These polymers are well suited for extrusion, blow molding, injection molding and the like.

The polymerization reaction can be conducted by contacting monomer or monomers, e.g., ethylene alone or with one or more other olefins, and in the substantial absence of catalyst poisons such as moisture and air, with a catalytic amount of the supported organometallic catalyst at a temperature and at a pressure sufficient to initiate the polymerization reaction. If desired, an inert organic solvent can be used as a diluent and to facilitate materials handling if the polymerization reaction is conducted with the reactants in the liquid phase, e.g. in a particle form (slurry) or solution process. The reaction can also be conducted with reactants in the vapor phase, e.g., in a fluidized bed arrangement in the absence of a solvent but, if desired, in the presence of an inert gas such as nitrogen.

The polymerization reaction is carried out at temperatures of from 30° C. or less to 200° C. or more, depending to a great extent on the operating pressure, the pressure of the olefin monomers, and the particular catalyst being used and its concentration. Naturally, the selected operating temperature is also dependent upon the desired polymer melt index since temperature is a factor in adjusting the molecular weight of the polymer. Typically, the temperature used is from 30° C. to 100° C. in a conventional slurry or "particle forming" process or from 100° C. to 150° C. in a "solution forming" process. A temperature of from 70° C. to 110° C. can be employed for fluidized bed processes.

The pressure to be used in the polymerization reactions can be any pressure sufficient to initiate the polymerization of the monomer(s) to high molecular weight polymer. The pressure, therefore, can range from sub-atmospheric pressures, using an inert gas as diluent, to super-atmospheric pressures of up to about 30,000 psig (206.8 MPa) or more, for example from atmospheric (0 psig) up to 1000 psig (6.89 MPa). As a general rule, a pressure of 20 to 800 psig (138 kPa to 5.52 MPa) is desirable.

The selection of an inert organic solvent medium to be employed in the solution or slurry process is not too critical, but the solvent should be inert to the supported organometallic catalyst and olefin polymer produced, and should be stable at the reaction temperature used. It is not necessary, however, that the inert organic solvent medium also serves as a solvent for the polymer to be produced. Among the inert organic solvents applicable for such purposes can be mentioned saturated aliphatic hydrocarbons having from 3 to 12 carbon atoms such as hexane, heptane, pentane, isooctane, purified kerosene and the like, saturated cycloaliphatic hydrocarbons having from 5 to 12 carbon atoms such as cyclohexane, cyclopentane, dimethylcyclopentane and methylcyclohexane and the like and aromatic hydrocarbons having from 6 to 12 carbon atoms such as benzene, toluene, xylene, and the like. Particularly desirable solvent media are cyclohexane, pentane, hexane and heptane.

Hydrogen can be introduced into the polymerization reaction zone in order to decrease the molecular weight of the polymers produced (i.e., give a much higher melt index). Partial pressure of hydrogen when hydrogen is used can be within the range of from 5 to 100 psig (34 to 689 kPa), e.g., from 25 to 75 psig (172 to 517 kPa). The melt indices of the polymers produced in accordance with this disclosure can range from 0.1 to 70 or even higher.

More detailed description of suitable polymerization conditions including examples of particle form, solution and fluidized bed polymerization arrangements are found in U.S. Pat. Nos. 3,709,853 and 4,086,408.

Condensation of Alcohols

SSZ-96 can be used to condense lower aliphatic alcohols having 1 to 10 carbon atoms to a gasoline boiling point hydrocarbon product comprising mixed aliphatic and aromatic hydrocarbons. The process disclosed in U.S. Pat. No. 3,894,107 describes the typical conditions used in this process.

The catalyst can be in the hydrogen form or can be base-exchanged or impregnated to contain an ammonium or a metal cation component, typically in the range of from 0.05 to 5 wt. %. The metal cations that can be present include any of the metals of Groups 1-10 of the Periodic Table. However, in the case of Group 1 metals, the cation content should in no case be so large as to effectively inactivate the catalyst, nor should the exchange be such as to eliminate all acidity. There can be other processes involving treatment of oxygenated substrates where a basic catalyst is desired.

Partial Oxidation of Low Value Hydrocarbons

The partial oxidation of low value hydrocarbons such as alkanes and alkenes into high value products such as alcohols and epoxides is of great commercial interest. These oxidation products are not only valuable as is, but also as intermediates for specialty chemicals including pharmaceuticals and pesticides.

U.S. Pat. No. 4,410,501 discloses a titanium-containing analogue of the all-silica ZSM-5 molecular sieve. This material (known as "TS-1") has been found to be useful in catalyzing a wide range of partial oxidation chemistries, for example the production of catechol and hydroquinone from phenol and hydrogen peroxide ($H_2O_2$) and the manufacture of propylene oxide and cyclohexanone oxime from propylene and cyclohexanone, respectively. In addition, TS-1 can be used to catalyze the reaction of alkanes and aqueous $H_2O_2$ to form alcohols and ketones (see, e.g., D. R. C. Huybrechts et al., *Nature* 1990, 345, 240-242; and T. Tatsumi et al., *J. Chem. Soc. Chem. Commun.* 1990, 476-477).

TS-1 has many salient features, other than its catalytic abilities, which make it attractive as a commercial catalyst. Most importantly, it is a solid. This allows for easy separation from the reactants and products (typically liquids) by simple, inexpensive filtration. Moreover, this solid has high thermal stability and a very long lifetime. Calcination in air at moderate temperatures (550° C.) restores the material to its original catalytic ability. TS-1 performs best at mild temperatures (<100° C.) and pressures (101 kPa). The oxidant used for reactions catalyzed by TS-1 is aqueous $H_2O_2$, which is important because aqueous $H_2O_2$ is relatively inexpensive and its by-product is water. Hence, the choice of oxidant is favorable from both a commercial and environmental point of view.

While a catalyst system based on TS-1 has many useful features, it has one serious drawback. The zeolite structure of TS-1 includes a regular system of pores which are formed by nearly circular rings of ten silicon atoms (called 10-membered rings, or simply "10 rings") creating pore diameters of approximately 5.5 Å (0.55 nm). This small size results in the exclusion of molecules larger than 5.5 Å. Because the catalytically active sites are located within the pores of the zeolite, any exclusion of molecules from the pores results in poor catalytic activity.

SSZ-96 containing titanium oxide (Ti-SSZ-96) is useful as a catalyst in oxidation reactions, particularly in the oxidation of hydrocarbons. Examples of such reactions include the epoxidation of olefins, the oxidation of alkanes, and the oxidation of sulfur-containing, nitrogen-containing or phosphorus-containing compounds.

The amount of Ti-SSZ-96 catalyst employed is not critical, but should be sufficient so as to substantially accomplish the desired oxidation reaction in a practicably short period of time (i.e., a catalytically effective amount). The optimum quantity of catalyst will depend upon a number of factors including reaction temperature, the reactivity and concentration of the substrate, hydrogen peroxide concentration, type and concentration of organic solvent, as well as the activity of the catalyst. Typically, however, the amount of catalyst will be from 0.001 to 10 g/mol of substrate. Typically, the Ti-SSZ-96 is thermally treated (calcined) prior to use as a catalyst.

The oxidizing agent employed in the oxidation processes disclosed herein is a hydrogen peroxide source such as hydrogen peroxide or a hydrogen peroxide precursor (i.e., a compound which under the oxidation reaction conditions is capable of generating or liberating $H_2O_2$).

The amount of $H_2O_2$ relative to the amount of substrate is not critical, but must be sufficient to cause oxidation of at least some of the substrate. Typically, the molar ratio of $H_2O_2$ to substrate is from 100:1 to 1:100, e.g., from 10:1 to 1:10. When the substrate is an olefin containing more than one carbon-carbon double bond, additional hydrogen peroxide can be required. Theoretically, one equivalent of hydrogen peroxide is required to oxidize one equivalent of a mono-unsaturated substrate, but it can be desirable to employ an excess of one reactant to optimize selectivity to the epoxide. In particular, the use of a moderate to large excess (e.g., 50 to 200%) of olefin relative to $H_2O_2$ can be advantageous for certain substrates.

If desired, a solvent can additionally be present during the oxidation reaction in order to dissolve the reactants other than the Ti-SSZ-96, to provide better temperature control, or to favorably influence the oxidation rates and selectivities. The solvent, if present, can comprise from 1 to 99 wt. % of the total oxidation reaction mixture and is desirably selected such that it is a liquid at the oxidation reaction temperature. Organic compounds having boiling points at atmospheric pressure of from 50° C. to 150° C. are generally desirable for use. Excess hydrocarbon can serve as a solvent or diluent. Illustrative examples of other suitable solvents include ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, tert-butyl alcohol, alpha-methyl benzyl alcohol, cyclohexanol). More than one type of solvent can be utilized. Water can also be employed as a solvent or diluent.

The reaction temperature is not critical, but should be sufficient to accomplish substantial conversion of the substrate within a reasonably short period of time. It is generally advantageous to carry out the reaction to achieve as high a hydrogen peroxide conversion as possible, typically at least 50%, e.g., at least 90% or at least 95%, consistent with reasonable selectivities. The optimum reaction temperature will be influenced by catalyst activity, substrate reactivity, reactant concentrations, and type of solvent employed, among other factors, but typically will be in a range of from 0° C. to 150° C., e.g., from 25° C. to 120° C. Reaction or residence times from one minute to 48 hours (e.g., from ten minutes to 8 hours) will typically be appropriate, depending upon the above-identified variables. Although sub-atmospheric pressures can be employed, the reaction is typically performed at atmospheric or at elevated pressure (typically, between 101 kPa and 10 MPa), especially when the boiling point of the substrate is below the oxidation reaction temperature. Generally, it is desirable to pressurize the reaction vessel sufficiently to maintain the reaction components as a liquid phase mixture. Most (over 50%) of the substrate should desirably be present in the liquid phase.

The oxidation process of this disclosure can be carried out in a batch, continuous, or semi-continuous manner using any appropriate type of reaction vessel or apparatus such as a fixed bed, transport bed, fluidized bed, stirred slurry, or CSTR reactor. The reactants can be combined all at once or sequentially. For example, the hydrogen peroxide or hydrogen peroxide precursor can be added incrementally to the reaction zone. The hydrogen peroxide could also be generated in situ within the same reactor zone where oxidation is taking place.

Once the oxidation has been carried out to the desired degree of conversion, the oxidized product can be separated and recovered from the reaction mixture using any appropriate technique such as fractional distillation, extractive distillation, liquid-liquid extraction, crystallization, or the like.

Olefin Epoxidation

One of the oxidation reactions for which Ti-SSZ-96 is useful as a catalyst is the epoxidation of olefins. The olefin substrate epoxidized in the process of this disclosure can be any organic compound having at least one ethylenically unsaturated functional group (i.e., a carbon-carbon double bond) and can be a cyclic, branched or straight-chain olefin. The olefin can contain aryl groups (e.g., phenyl, naphthyl). Typically, the olefin is aliphatic in character and contains from 2 to 20 carbon atoms. The use of light (low-boiling) $C_2$ to $C_{10}$ mono-olefins is especially advantageous.

More than one carbon-carbon double bond can be present in the olefin, i.e., dienes, trienes and other polyunsaturated substrates can be used. The double bond can be in a terminal or internal position in the olefin or can alternatively form part of a cyclic structure (as in cyclooctene, for example). Other examples of suitable substrates include unsaturated fatty acids or fatty acid derivatives such as esters.

The olefin can contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this disclosure include ethylene, propylene, the butenes (i.e., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinyl cyclohexane, vinyl cyclohexene, allyl chloride, the dichlorobutenes, allyl alcohol, allyl carbonate, allyl acetate, alkyl acrylates and methacrylates, diallyl maleate, diallyl phthalate, and unsaturated fatty acids, such as oleic acid, linolenic acid, linoleic acid, erucic acid, palmitoleic acid, and ricinoleic acid and their esters (including mono-, di-, and triglyceride esters) and the like.

Olefins which are especially useful for epoxidation are the $C_2$ to $C_{20}$ olefins having the general structure (3):

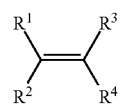

(3)

wherein $R^1$, $R^2$, $R^3$ and $R^4$ are the same or different and are selected from the group consisting of hydrogen and $C_1$ to $C_{18}$ alkyl.

Mixtures of olefins can be epoxidized and the resulting mixtures of epoxides either employed in the mixed form or separated into the different component epoxides.

The present disclosure further provides a process for oxidation of hydrocarbons comprising contacting the hydrocarbon with hydrogen peroxide in the presence of a catalytically effective amount of Ti-SSZ-96 for a time and at a temperature effective to oxidize the hydrocarbon.

Oxygenate Conversion

The disclosed herein comprises a process for catalytic conversion of a feedstock comprising one or more oxygenates comprising alcohols and ethers to a hydrocarbon product containing light olefins, i.e., $C_2$, $C_3$ and/or $C_4$ olefins. The feedstock is contacted with SSZ-96 at effective process conditions to produce light olefins. The term "oxygenate" as used herein designates compounds such as alcohols, ethers, and carbonyl compounds (e.g., aldehydes, ketones, carboxylic acids). The oxygenate can contain from 1 to 10 carbon atoms, e.g., from 1 to 4 carbon atoms. The representative oxygenates include lower straight chained branched alcohols, and their unsaturated counterparts. Particularly suitable oxygenate compounds are methanol, dimethyl ether, and mixtures thereof.

The process disclosed can be conducted in the presence of one or more diluents which can be present in the oxygenate feed in an amount of from 1 to 99 mole %, based on the total number of moles of all feed and diluent components. Diluents include helium, argon, nitrogen, carbon monoxide, carbon dioxide, hydrogen, water, paraffins, hydrocarbons (such as methane and the like), aromatic compounds, or mixtures thereof. U.S. Pat. Nos. 4,677,242; 4,861,938; and 4,677,242 emphasize the use of a diluent to maintain catalyst selectivity toward the production of light olefins, particularly ethylene.

The oxygenate conversion is desirably conducted in the vapor phase such that the oxygenate feedstock is contacted in a vapor phase in a reaction zone with SSZ-96 at effective process conditions to produce hydrocarbons, i.e., an effective temperature, pressure, WHSV and, optionally, an effective amount of diluent. The process is conducted for a period of time sufficient to produce the desired light olefins. In general, the residence time employed to produce the desired product can vary from seconds to a number of hours. It will be readily appreciated that the residence time will be determined to a significant extent by the reaction temperature, the molecular sieve catalyst, the WHSV, the phase (liquid or vapor) and process design characteristics. The oxygenate feedstock flow rate affects olefin production. Increasing the feedstock flow rate increases WHSV and enhances the formation of olefin production relative to paraffin production. However, the enhanced olefin production relative to paraffin production is offset by a diminished conversion of oxygenate to hydrocarbons.

Light olefin products will form, although not necessarily in optimum amounts, at a wide range of pressures, including but not limited to autogenous pressures and pressures in the range from 0.1 kPa to 10 MPa. Conveniently, the pressure can be in the range from 7 kPa to 5 MPa, e.g., from 50 kPa to 1 MPa. The foregoing pressures are exclusive of diluents, if any are present, and refer to the partial pressure of the feedstock as it relates to oxygenate compounds and/or mixtures thereof. Lower and upper extremes of pressure can adversely affect selectivity, conversion, coking rate, and/or reaction rate; however, light olefins such as ethylene and/or propylene still may form.

The temperature which can be employed in the oxygenate conversion process can vary over a wide range depending, at least in part, on the molecular sieve catalyst. In general, the process can be conducted at an effective temperature of from 200° C. to 700° C. At the lower ends of the temperature range, and thus generally at a lower rate of reaction, the formation of the desired light olefins can become low. At the upper ends of the range, the process cannot form an optimum amount of light olefins and catalyst deactivation can be rapid.

The molecular sieve catalyst can be incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and can or cannot be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve desirably comprises from 1 to 99 wt. % (e.g., from 5 to 90 wt. % or from 10 to 80 wt. %) of the total composition.

Acylation

SSZ-96 can be used in a catalyst for acylating an aromatic substrate $ArH_k$, where k is at least 1, by reacting the aromatic substrate with an acylating agent in the presence of the catalyst. The product of the acylation reaction is $ArH_{k-1}COR^5$ where $R^5$ is an organic radical.

Examples of the aromatic substrate include, but are not limited to, benzene, toluene, anisole and 2-naphthol. Examples of the acylating agent included, but are not limited to, carboxylic acid derivatives, carboxylic acids, acid anhydrides, esters, and acyl halides.

Reaction conditions are known in the art (see, e.g., U.S. Pat. Nos. 6,459,000; 6,548,722; and 6,630,606). Typically, the acylation reaction is conducted with a weight ratio of the catalyst to the acylating agent of from 0.03 to 0.5, a mole ratio of aromatic substrate to acylating agent of from 1.0 to 20, a reaction temperature of from 20° C. to 200° C., a reaction pressure of from 101 to 507 kPa, and a reaction time of from 0.05 to 20 h.

Synthesis of Amines

SSZ-96 can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

The catalyst is used in its acid form. Acid forms of molecular sieves can be prepared by a variety of techniques. Desirably, the molecular sieve used to prepare dimethylamine will be in the hydrogen form, or have an alkali or alkaline earth metal, such as Na, K, Rb, or Cs, ion-exchanged into it.

The process disclosed herein involves reacting methanol, dimethyl ether, or a mixture thereof and ammonia in amounts sufficient to provide a carbon/nitrogen (C/N) ratio of from 0.2 to 1.5, e.g., from 0.5 to 1.2. The reaction is conducted at a temperature of from 250° C. to 450° C., e.g., from 300° C. to 400° C. Reaction pressures can vary from 7 to 7000 kPa, e.g., from 70 to 3000 kPa. A methanol and/or dimethyl ether space time of from 0.01 to 80 $h^{-1}$ (e.g., from 0.10 to 1.5 $h^{-1}$) is typically used. This space time is calculated as the mass of catalyst divided by the mass flow rate of methanol/dimethyl ether introduced into the reactor.

Beckmann Rearrangement

SSZ-96 can be used as a catalyst in the transformation of oximes (such as cyclohexanone oxime) to amides (such as epsilon-caprolactam), also known as a Beckmann rearrangement. The Beckmann rearrangement is shown below (where sulfuric acid is used instead of a molecular sieve catalyst).

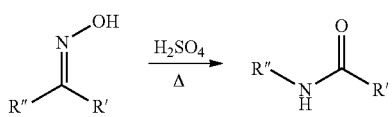

Amides, and in particular epsilon-caprolactam, are known in literature as important intermediates for chemical syntheses and as raw materials for the preparation of polyamide resins.

Caprolactam is produced industrially by cyclohexanone oxime rearrangement in liquid phase using sulfuric acid or oleum. The rearranged product is neutralized with ammonia causing the joint formation of ammonium sulfate. This technology has numerous problems linked to the use of sulfuric acid, to the formation of high quantities of ammonium sulfate, with relative problems of disposal, corrosion of the equipment owing to the presence of acid vapors, etc.

Alternative processes have been proposed in the literature for the catalytic rearrangement of cyclohexanone oxime into caprolactam, in which solids of an acid nature are used, as catalysts, selected from derivatives of boric acid, zeolites, non-zeolitic molecular sieves, solid phosphoric acid, mixed metal oxides, etc.

In particular, European Patent No. 234,088 describes a method for preparing caprolactam which comprises putting cyclohexanone oxime in gaseous state in contact with aluminosilicate zeolites such as ZSM-5, ZSM-11 or ZSM-23 having a constraint index of between 1 and 12, a $SiO_2/Al_2O_3$ mole ratio of at least 500 and an external acid functionality of less than 5 micro-equivalents/g.

With the aim of providing another method for the preparation of amides, and in particular of caprolactam, a new process has now been found which uses a catalyst comprising SSZ-96. The present disclosure therefore relates to a process for the preparation of amides via the catalytic rearrangement of oximes which comprises putting an oxime in the vapor phase in contact with a catalyst comprising a crystalline molecular sieve having a mole ratio of at least 10 of (1) at least one oxide of at least one tetravalent element to (2) one or more oxides selected from the group consisting of oxides of trivalent elements, pentavalent elements, and mixtures thereof, and having, in its calcined from, the X-ray diffraction lines of Table 6. The molecular sieve can have a mole ratio of at least 10 of (1) silicon oxide to (2) an oxide selected from boron oxide, aluminum oxide, gallium oxide, indium oxide, and mixtures thereof.

Other methods for converting oximes to amides via Beckmann rearrangement are disclosed in U.S. Pat. Nos. 4,883,915 and 5,942,613.

A desirable amide is epsilon-caprolactam (ε-caprolactam) and the desirable oxime is cyclohexanone oxime. In particular, the catalytic rearrangement of the cyclohexanone oxime takes place at a pressure of from 5 kPa to 1 MPa and at a temperature of from 250° C. and 500° C., e.g., from 300° C. to 450° C. More specifically, the cyclohexanone oxime, in vapor phase, is fed to the reactor containing the catalyst in the presence of a solvent and optionally an incondensable gas. The cyclohexanone oxime is dissolved in the solvent and the mixture thus obtained is then vaporized and fed to the reactor. The solvent should be essentially inert to the oxime and the amide, as well as the catalyst. Useful solvents include, but are not limited to, lower boiling hydrocarbons, alcohols and ethers.

Desirable solvents are of the type $R^6$—O—$R^7$ wherein $R^6$ is a $C_1$ to $C_4$ alkyl chain and $R^7$ can be a hydrogen atom or an alkyl chain containing a number of carbon atoms less than or equal to $R^6$. These solvents can be used alone or mixed with each other or combined with an aromatic hydrocarbon such as benzene or toluene. Alcohols with a $C_1$ to $C_2$ alkyl chain are particularly desirable.

The cyclohexanone oxime is fed to the rearrangement reactor with a weight ratio with respect to the catalyst which is such as to give a WHSV, expressed as kg of cyclohexanone oxime/kg of catalyst/time, of from 0.1 to 50 $h^{-1}$, e.g., from 0.5 to 20 $h^{-1}$.

The deterioration of the catalyst is due to the formation of organic residues which obstruct the pores of the catalyst and poison its active sites. The deterioration process is slow and depends on the operating conditions and in particular the space velocity, solvent, temperature, composition of the feeding. The catalytic activity however can be efficiently reintegrated by the combustion of the residues, by treatment in a stream of air and nitrogen at a temperature of from 450° C. to 600° C.

Gas Separation

SSZ-96 can be used to separate gasses. For example, it can be used to separate carbon dioxide from natural gas. Typically, the molecular sieve is used as a component in a membrane that is used to separate the gases. Examples of such membranes are disclosed in U.S. Pat. No. 6,508,860.

Treatment of Engine Exhaust (Cold Start Emissions)

Gaseous waste products resulting from the combustion of hydrocarbonaceous fuels, such as gasoline and fuel oils, comprise carbon monoxide, hydrocarbons and nitrogen oxides as products of combustion or incomplete combustion, and can pose a serious health problem with respect to pollution of the atmosphere. While exhaust gases from other carbonaceous fuel-burning sources, such as stationary engines, industrial furnaces, etc., contribute substantially to air pollution, the exhaust gases from automotive engines are a principal source of pollution. Because of these concerns, the U.S. Environmental Protection Agency has promulgated strict controls on the amounts of carbon monoxide, hydrocarbons and nitrogen oxides which automobiles can emit. The implementation of these controls has resulted in the use of catalytic converters to reduce the amount of pollutants emitted from automobiles.

In order to achieve the simultaneous conversion of carbon monoxide, hydrocarbon and nitrogen oxide pollutants, it has become the practice to employ catalysts in conjunction with air-to-fuel ratio control means which functions in response to a feedback signal from an oxygen sensor in the engine exhaust system. Although these three component control catalysts work quite well after they have reached operating temperature of about 300° C., at lower temperatures they are not able to convert substantial amounts of the pollutants. What this means is that when an engine and in particular an automobile engine is started up, the three component control catalyst is not able to convert the hydrocarbons and other pollutants to innocuous compounds.

Adsorbent beds have been used to adsorb the hydrocarbons during the cold start portion of the engine. Although the process typically will be used with hydrocarbon fuels, the present disclosure can also be used to treat exhaust streams from alcohol-fueled engines. The adsorbent bed is typically placed immediately before the catalyst. Thus, the exhaust stream is first flowed through the adsorbent bed and then through the catalyst. The adsorbent bed preferentially adsorbs hydrocarbons over water under the conditions present in the exhaust stream. After a certain amount of time, the adsorbent bed has reached a temperature (typically about 150° C.) at which the bed is no longer able to remove hydrocarbons from the exhaust stream. That is, hydrocarbons are actually desorbed from the adsorbent bed instead of being adsorbed. This regenerates the adsorbent bed so that it can adsorb hydrocarbons during a subsequent cold start. The use of adsorbent beds to minimize hydrocarbon emissions during a cold start engine operation is known in the art. See, for example, U.S. Pat. Nos. 2,942,932; 3,699,683; and 5,078,979.

As stated, this disclosure generally relates to a process for treating an engine exhaust stream and, in particular, to a process for minimizing emissions during the cold start operation of an engine. The engine consists of any internal or external combustion engine which generates an exhaust gas stream containing noxious components or pollutants including unburned or thermally degraded hydrocarbons or similar organics. Other noxious components usually present in the exhaust gas include nitrogen oxides and carbon monoxide. The engine can be fueled by a hydrocarbonaceous fuel. As used herein, the term "hydrocarbonaceous fuel" includes hydrocarbons, alcohols and mixtures thereof. Examples of hydrocarbons which can be used to fuel the engine are the mixtures of hydrocarbons which make up gasoline or diesel fuel. The alcohols which can be used to fuel engines include ethanol and methanol. Mixtures of alcohols and mixtures of alcohols and hydrocarbons can also be used. The engine can be a jet engine, gas turbine, internal combustion engine, such as an automobile, truck or bus engine, a diesel engine or the like. The process of this disclosure is particularly suited for an internal combustion engine mounted in an automobile.

When the engine is started up, it produces a relatively high concentration of hydrocarbons in the engine exhaust gas stream as well as other pollutants. Pollutants will be used herein to collectively refer to any unburned fuel components and combustion byproducts found in the exhaust stream. For example, when the fuel is a hydrocarbon fuel, hydrocarbons, nitrogen oxides, carbon monoxide and other combustion byproducts will be found in the engine exhaust gas stream. The temperature of this engine exhaust stream is relatively cool, generally below 500° C. and typically in the range of from 200° C. to 400° C. This engine exhaust stream has the above characteristics during the initial period of engine operation, typically for the first 30 to 120 seconds after startup of a cold engine. The engine exhaust stream will typically contain from 500 to 1000 ppm hydrocarbons by volume.

In one embodiment, the engine exhaust gas stream which is to be treated is flowed over a combination of molecular sieves which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere. The combination of molecular sieves includes SSZ-96 in combination with: (1) a small pore crystalline molecular sieve or mixture of molecular sieves having pores no larger than 8-membered rings selected from the group consisting of SSZ-13, SSZ-16, SSZ-36, SSZ-39. SSZ-50, SSZ-52 and SSZ-73 and having a mote ratio of at least 10 of (a) at least one oxide of at least one tetravalent element to (b) one or more oxides selected from the group consisting of oxides of trivalent elements, pentavalent elements, and mixtures thereof; and/or (2) a large pore crystalline molecular sieve having pores at least as large as 10-membered rings selected from the group consisting of SSZ-26, SSZ-33, SSZ-64, zeolite Beta, CIT-1, CIT-6 and ITQ-4 and having a mole ratio of at least 10 of (a) at least one oxide of at least one tetravalent element to (b) one or more oxides selected from the group consisting of oxides of trivalent elements, pentavalent elements, and mixtures thereof.

The engine exhaust gas stream which is to be treated is flowed over a molecular sieve bed comprising molecular sieve SSZ-96 as a first exhaust stream. The first exhaust stream which is discharged from the molecular sieve bed is now flowed over a catalyst to convert the pollutants contained in the first exhaust stream to innocuous components and provide a treated exhaust stream which is discharged into the atmosphere. It is understood that prior to discharge into the atmosphere, the treated exhaust stream can be flowed through a muffler or other sound reduction apparatus well known in the art.

The catalyst which is used to convert the pollutants to innocuous components is usually referred to in the art as a three-component control catalyst because it can simultaneously oxidize any residual hydrocarbons present in the first exhaust stream to carbon dioxide and water, oxidize any residual carbon monoxide to carbon dioxide and reduce any residual nitric oxide to nitrogen and oxygen. In some cases the catalyst cannot be required to convert nitric oxide to nitrogen and oxygen, e.g., when an alcohol is used as the fuel. In this case the catalyst is called an oxidation catalyst. Because of the relatively low temperature of the engine exhaust stream and the first exhaust stream, this catalyst does not function at a very high efficiency, thereby necessitating the molecular sieve bed.

When the molecular sieve bed reaches a sufficient temperature, typically from 150° C. to 200° C., the pollutants which are adsorbed in the bed begin to desorb and are carried by the first exhaust stream over the catalyst. At this point the catalyst has reached its operating temperature and is therefore capable of fully converting the pollutants to innocuous components.

The adsorbent bed used in this disclosure can be conveniently employed in particulate form or the adsorbent can be deposited onto a solid monolithic carrier. When particulate form is desired, the adsorbent can be formed into shapes such as pills, pellets, granules, rings, spheres, etc. In the employment of a monolithic form, it is usually most convenient to employ the adsorbent as a thin film or coating deposited on an inert carrier material which provides the structural support for the adsorbent. The inert carrier material can be any refractory material such as ceramic or metallic materials. It is desirable that the carrier material be unreactive with the adsorbent and not be degraded by the gas to which it is exposed. Examples of suitable ceramic materials include sillimanite, petalite, cordierite, mullite, zircon, zircon mullite, spondumene, alumina-titanate, etc. Additionally, metallic materials which are within the scope of this disclosure include metals and alloys as disclosed in U.S. Pat. No. 3,920,583 which are oxidation resistant and are otherwise capable of withstanding high temperatures.

The carrier material can best be utilized in any rigid unitary configuration which provides a plurality of pores or channels extending in the direction of gas flow. The configuration can be a honeycomb configuration. The honeycomb structure can be used advantageously in either unitary form, or as an arrangement of multiple modules. The honeycomb structure is usually oriented such that gas flow is generally in the same direction as the cells or channels of the honeycomb structure. For a more detailed discussion of monolithic structures, refer to U.S. Pat. Nos. 3,767,453 and 3,785,998.

The molecular sieve is deposited onto the carrier by any convenient way well known in the art. A desirable method involves preparing a slurry using the molecular sieve and coating the monolithic honeycomb carrier with the slurry. The slurry can be prepared by means known in the art such as combining the appropriate amount of the molecular sieve and a binder with water. This mixture is then blended by using means such as sonication, milling, etc. This slurry is used to coat a monolithic honeycomb by dipping the honeycomb into the slurry, removing the excess slurry by draining or blowing out the channels, and heating to about 100° C. If the desired loading of molecular sieve is not achieved, the above process can be repeated as many times as required to achieve the desired loading.

Instead of depositing the molecular sieve onto a monolithic honeycomb structure, the molecular sieve can be formed into a monolithic honeycomb structure by means known in the art.

The adsorbent can optionally contain one or more catalytic metals dispersed thereon. The metals which can be dispersed on the adsorbent are the noble metals which consist of platinum, palladium, rhodium, ruthenium, and mixtures thereof. The desired noble metal can be deposited onto the adsorbent, which acts as a support, in any suitable manner well known in the art. One example of a method of dispersing the noble metal onto the adsorbent support involves impregnating the adsorbent support with an aqueous solution of a decomposable compound of the desired noble metal or metals, drying the adsorbent which has the noble metal compound dispersed on it and then calcining in air at a temperature of 400° C. to 500° C. for a time of from 1 to 4 hours. By decomposable compound is meant a compound which upon heating in air gives the metal or metal oxide. Examples of the decomposable compounds which can be used are set forth in U.S. Pat. No. 4,791,091. Examples of decomposable compounds are chloroplatinic acid, rhodium trichloride, chloropalladic acid, hexachloroiridate(IV) acid and hexachlororuthenate(IV). It is typical that the noble metal be present in an amount ranging from 0.01 to 4 wt. % of the adsorbent support. Specifically, in the case of platinum and palladium the range is from 0.1 to 4 wt. %, while in the case of rhodium and ruthenium the range is from 0.01 to 2 wt. %.

These catalytic metals are capable of oxidizing the hydrocarbon and carbon monoxide and reducing the nitric oxide components to innocuous products. Accordingly, the adsorbent bed can act both as an adsorbent and as a catalyst.

The catalyst which is used in this disclosure is selected from any three component control or oxidation catalyst well known in the art. Examples of catalysts are those described in U.S. Pat. Nos. 4,528,279; 4,760,044; 4,791,091; 4,868,148; and 4,868,149. Desirable catalysts well known in the art are those that contain platinum and rhodium and optionally palladium, while oxidation catalysts usually do not contain rhodium. Oxidation catalysts usually contain platinum and/or palladium metal. These catalysts can also contain promoters and stabilizers such as barium, cerium, lanthanum, nickel, and iron. The noble metals promoters and stabilizers are usually deposited on a support such as alumina, silica, titania, zirconia, alumino silicates, and mixtures thereof with alumina being desirable. The catalyst can be conveniently employed in particulate form or the catalytic composite can be deposited on a solid monolithic carrier with a monolithic carrier being desirable. The particulate form and monolithic form of the catalyst are prepared as described for the adsorbent above. The molecular sieve used in the adsorbent bed is SSZ-96.

Reduction of Oxides of Nitrogen

SSZ-96 can be used for the catalytic reduction of the oxides of nitrogen in a gas stream. Typically, the gas stream also contains oxygen, often a stoichiometric excess thereof. Also, the molecular sieve can contain a metal or metal ions within or on it which are capable of catalyzing the reduction of the nitrogen oxides. Examples of such metals or metal ions include lanthanum, chromium, manganese, iron, cobalt, rhodium, nickel, palladium, platinum, copper, zinc, and mixtures thereof.

One example of such a process for the catalytic reduction of oxides of nitrogen in the presence of a zeolite is disclosed in U.S. Pat. No. 4,297,328. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

EXAMPLES

The following illustrative examples are intended to be non-limiting.

Example 1

Synthesis of 1-butyl-1-methyl-octahydroindolium cation

Synthesis of 1-methyl-octahydroindole: To a solution of 100 g of 1-methylindole in absolute ethanol in a 600 mL autoclave, 5 g of $PtO_2$ and 10 mL of $H_2SO_4$ were added. The mixture was sealed and pressurized with hydrogen to 1500 psig. The reaction mixture was heated at 100° C. overnight while stirring at about 400 rpm. The reaction mixture was pressurized again to 1500 psig and heated at 100° C. for several more hours. The reaction mixture was cooled and filtered to remove the catalyst. The filtrate was concentrated on a rotary evaporator to remove ethanol. The residue was neutralized with sodium hydroxide solution and left to stir at room temperature for about 30 minutes. The solution was transferred to a reparatory funnel and extracted with diethyl ether. The ether layer was dried over anhydrous $MgSO_4$, filtered and concentrated at reduced pressure on a rotary evaporator to give 93.0 g of the product, 1-methyl-octahydroindole, as a yellow oil. The product was confirmed by NMR.

Synthesis of 1-butyl-1-methyl-octahydroindolium hydroxide: 20 g (0.14 mmol) of 1-methyl-octahydroindole was mixed with 53 g (0.29 mmol) of 1-iodobutane in 300 mL of methanol. The reaction mixture was heated at reflux for 72 hours. Then, an additional 0.5 mol equivalent of 1-iodobutane was added and the reaction mixture was heated for an additional 12 hours. The reaction mixture was cooled and the solvent removed on a rotary evaporator to give an off-white powder which was used without further purification. The quaternization afforded 39.4 g (86% yield) of 1-butyl-1-methyl-octahydroindolium iodide. The obtained 1-butyl-1-methyl-octahydroindolium iodide (18.15 g) was dissolved in 56 g of deionized water. To this solution, 70 g of BIO-RAD AG® 1-X8 ion exchange resin was added and the slurry was gently stirred at room temperature overnight. The solution was filtered and the filtrate analyzed for hydroxide content by titration of a small aliquot with dilute HCl. The exchange afforded 1-butyl-1-methyl-octahydroindolium hydroxide in 87% yield.

Scheme 1 below depicts the synthesis of the SDA.

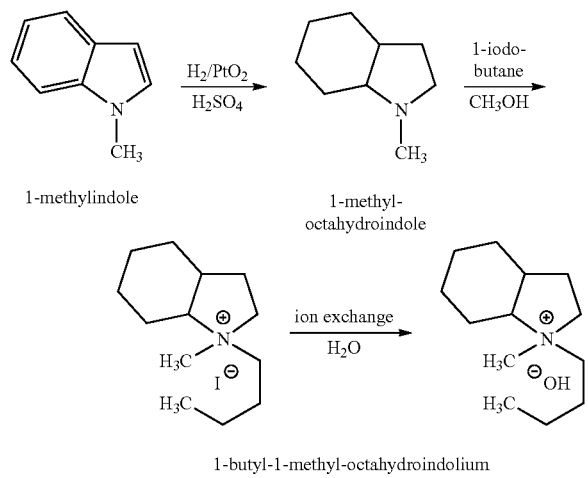

Example 2

Synthesis of SSZ-96

A 23 mL Teflon liner was charged with 4.9 g of 1-butyl-1-methyl-octahydroindolium hydroxide solution (3 mmol of cation and 3 mmol of hydroxide), 0.75 g of 1N NaOH solution, 0.75 g of CAB-O-SIL® M-5 fumed silica (Cabot Corporation), 0.25 g of LZ-210 zeolite and 2 g of deionized water. The resulting gel mixture was stirred thoroughly until a homogeneous solution was obtained. The Teflon liner containing the resulting gel mixture was capped off and placed in a stainless steel Parr autoclave. The autoclave was affixed onto a spit rotating at 43 rpm in an oven at 170° C. The gel mixture was heated for 6 days after which the reaction was completed to give a settled powder and a clear solution. The reaction mixture was filtered and washed thoroughly with deionized water. The solids were dried in air overnight and then dried in an oven at 120° C. for 2 hours. The obtained solids (0.9 g) were analyzed by powder XRD. The powder XRD pattern of the resulting product is shown in FIG. 1 and indicates that the material was unique.

Example 3

Calcination of SSZ-96

Figure 2:
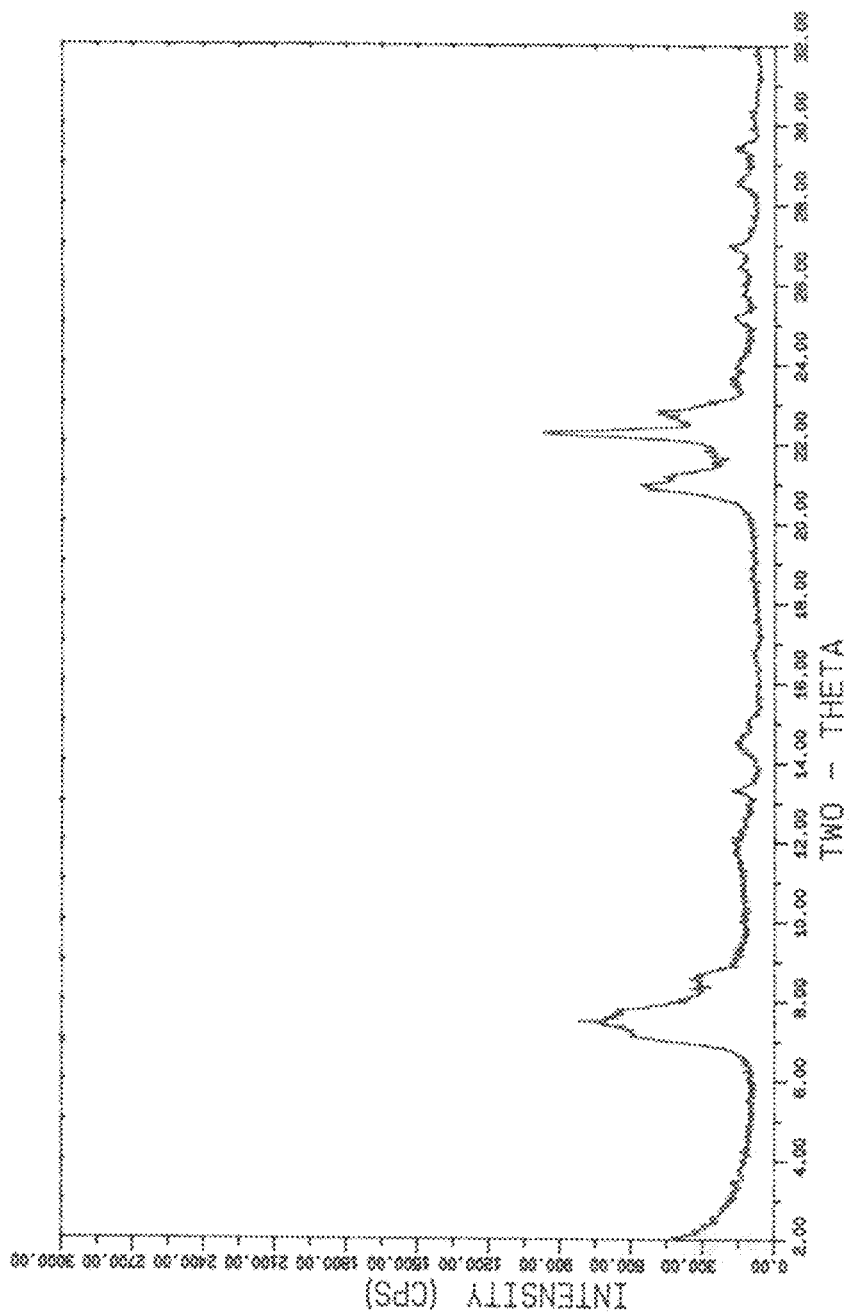
FIG. 2 is a powder XRD pattern of the calcined molecular sieve prepared in Example 3.

The as-synthesized product from Example 2 was calcined in air in a muffle furnace from room temperature to 120° C. at a rate of 1° C./minute and held at 120° C. for 2 hours. The temperature was then ramped up to 540° C. at a rate of 1° C./minute and held at 540° C. for 5 hours. The temperature was then increased at the same rate (1° C./min) to 595° C. at held at 595° C. for 5 hours. The powder XRD pattern of the calcined molecular sieve is shown in FIG. 2 and indicates that the material remains stable after calcination to remove the organic SDA.

The micropore volume and external surface area of calcined SSZ-96 were then measured by nitrogen physisorption using the BET method. The measured micropore volume was 0.13 cm$^3$/g, the external surface area was 59.7 m$^2$/g and the BET surface area was 330.7 m$^2$/g.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A process for converting hydrocarbons comprising contacting a hydrocarbonaceous feed at hydrocarbon converting conditions with a catalyst comprising a molecular sieve having a mole ratio of at least 10 of (1) at least one oxide of at least one tetravalent element to (2) one or more oxides selected from the group consisting of trivalent elements, pentavalent elements, and mixtures thereof, and having, in its calcined form, an X-ray diffraction pattern substantially as shown in the following Table:

| 2-Theta | d-spacing (nm) | Relative Intensity |
|---|---|---|
| 7.50 ± 0.20 | 1.178 | VS |
| 8.52 ± 0.20 | 1.037 | M |
| 14.50 ± 0.20 | 0.610 | W |
| 20.86 ± 0.20 | 0.425 | S |
| 22.26 ± 0.20 | 0.399 | VS |
| 22.76 ± 0.20 | 0.390 | S |
| 23.60 ± 0.20 | 0.377 | W |
| 24.02 ± 0.20 | 0.370 | W |
| 25.16 ± 0.20 | 0.354 | W |
| 26.40 ± 0.20 | 0.337 | W |
| 26.94 ± 0.20 | 0.331 | W |
| 28.57 ± 0.20 | 0.312 | W |
| 29.41 ± 0.20 | 0.303 | W. |

2. The process of claim 1, wherein the molecular sieve has a mole ratio of at least 10 of (1) silicon oxide to (2) and oxide selected from boron oxide, aluminum oxide, gallium oxide, indium oxide, and mixtures thereof.

3. The process of claim 1, wherein the molecular sieve has a composition, as-synthesized and in its anhydrous form, in terms of mole ratios, as follows:

| | |
|---|---|
| $TO_2/X_2O_n$ | $\geq 10$ |
| $Q/TO_2$ | 0.05 to 0.5 |
| $M/TO_2$ | 0.01 to 0.6 | wherein:
(1) T is selected from the group consisting of tetravalent elements from Groups 4-14 of the Periodic Table, and mixtures thereof;
(2) X is selected from the group consisting of trivalent and pentavalent elements from Groups 3-13 of the Periodic Table, and mixtures thereof;
(3) n equals the valence state of X;
(4) Q is a 1-butyl-1-methyl-octahydroindolium cation; and
(5) M is selected from the group consisting of elements from Groups 1 and 2 of the Periodic Table.

4. The process of claim 3, wherein T is selected from the group consisting of Si, Ge, and mixtures thereof.

5. The process of claim 4, wherein T is Si.

6. The process of claim 3, wherein X is selected from the group consisting of B, Al, Ga, In, and mixtures thereof.

7. The process of claim 3, wherein T is Si and X is Al.

8. The process of claim 1, wherein the process is a process selected from the group consisting of hydrocracking, dewaxing, catalytic cracking, aromatics formation, isomerization, alkylation and transalkylation, conversion of paraffins to aromatics, isomerization of olefins, xylene isomerization, oligomerization, condensation of alcohols, methane upgrading and polymerization of 1-olefins.

9. The process of claim 8, wherein the process is a dewaxing process comprising contacting the catalyst with a hydrocarbon feedstock under dewaxing conditions.

10. The process of claim 1, wherein the process is a process for producing a $C_{20+}$ lube oil from a $C_{20+}$ olefin feed comprising isomerizing the olefin feed under isomerization conditions over the catalyst.

* * * * *